(12) United States Patent
Ishii

(10) Patent No.: US 6,761,922 B2
(45) Date of Patent: Jul. 13, 2004

(54) SWEETENER COMPOSITIONS CONTAINING ASPARTYL DIPEPTIDE ESTER COMPOUNDS

(75) Inventor: Shoichi Ishii, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/115,937

(22) Filed: Apr. 5, 2002

(65) Prior Publication Data

US 2003/0044502 A1 Mar. 6, 2003

Related U.S. Application Data

(63) Continuation of application No. PCT/JP00/06629, filed on Sep. 26, 2000.

(30) Foreign Application Priority Data

Oct. 5, 1999 (JP) .......................................... 11-284344
Oct. 5, 1999 (JP) .......................................... 11-284345

(51) Int. Cl.$^7$ .............................................. A23L 1/236
(52) U.S. Cl. ...................... 426/548; 426/573; 426/658; 560/41; 562/433

(58) Field of Search .................................. 426/548, 573, 426/658, 661; 560/40, 41; 562/409, 433, 442, 450

(56) References Cited

U.S. PATENT DOCUMENTS

| | | |
|---|---|---|
| 5,114,726 A | 5/1992 | Tsau et al. |
| 5,242,705 A | 9/1993 | Cailler et al. |
| 5,480,668 A | 1/1996 | Nofre et al. |
| 6,652,901 B2 * | 11/2003 | Ishii ........................... 426/548 |

FOREIGN PATENT DOCUMENTS

| | | |
|---|---|---|
| EP | 0 097 950 | 1/1984 |
| WO | 99/12954 | 3/1999 |

* cited by examiner

*Primary Examiner*—Leslie Wong
(74) *Attorney, Agent, or Firm*—Oblon, Spivak, McClelland, Maier & Neustadt, P.C.

(57) ABSTRACT

The present invention provides solid and liquid sweetening compositions with a high intensity sweetness containing aspartyl dipeptide ester compounds, processing of making the aspartyl dipeptide ester compounds, as well as food and beverages containing the compositions.

66 Claims, No Drawings

SWEETENER COMPOSITIONS CONTAINING ASPARTYL DIPEPTIDE ESTER COMPOUNDS

CROSS-REFERENCE TO RELATED APPLICATION

The present application is a continuation application of PCT/JP00/06629 filed Sep. 26, 2000, the entire contents of which are incorporated by reference. This application also claims priority to Japanese Patent Applications 11-284344 and 11-284345 both filed Oct. 5, 1999 and whose contents are incorporated by reference.

FIELD OF THE INVENTION

The present invention relates to a novel solid sweetener composition. In particular, a solid sweetener composition containing a novel aspartyl dipeptide ester compound, which has a high sweetness intensity. An example of such aspartyl dipeptide ester compounds is N-[N-[3-(3-hydroxy-4-methoxyphenyl) propyl]-L-α-aspartyl]-L-phenylalanine 1-methyl ester (referred to as "derivative 1").

In addition, the present invention relates to a novel liquid sweetener composition. In particular, a liquid sweetener composition of a solution, with at least one aspartyl dipeptide ester derivatives and which also contains at one of a sugar, a sugar alcohol, or an oligosaccharide as a stabilizer.

The present invention also provides a food, a beverage or other sweetened products using the same.

BACKGROUND OF THE INVENTION

It has been reported that the sweetness intensity of Neotame, which is a sweetener with a high intense sweetness is 10000 times that of sucrose by weight (refer to Japanese Patent Kohyo Publication JP-A-8-503206), and the sweetness intensity of Aspartame is 200 times that of sucrose by weight (refer to Japanese Patent Kokoku Publication JP-B-47-31031). These sweeteners have been commercially and research for additional applications is ongoing. While many other sweeteners with a high intense sweetness have been proposed, these sweeteners have many practical problems for use.

Therefore, a sweetener with a high intensity sweetness, which is different from the sweetness of conventional sweeteners is in demand, preferably such a sweetener should possess a high intense sweetness, with excellent sweetness quality, and physical properties (such as stability).

As a result of research to develop a sweet substance with a high intense sweetness, the present inventor previously found that an aspartyl dipeptide ester derivative represented by formula (2) had a high intense sweetness and was useful as a sweetener.

The present inventor has also found that the magnification of sweetness intensity of the derivative is extremely high, and that when the derivative is used directly in food, etc. in need of sweetness by sprinkling (as an example), the sweet taste is not homogeneous, which is not desired. Likewise, when a sweetener composition was prepared by mixing the aspartyl dipeptide derivative with a filler the powder form was not a homogeneous dispersion or mixture, which was not preferred due to the unbalanced sweetness.

Therefore, there is a need to develop a method whereby a sweetener composition is produced so that the composition has a homogeneous sweetness. Thus, it is an object of the present invention to develop a solid sweetener composition in which the derivative can be homogeneously dispersed and mixed.

In addition, as a result of further studies by the present inventor, the sweetness intensity of the aspartyl dipeptide ester derivative was confirmed to be extremely high—5000 to 50000 times, or more, compared to sucrose, and attempts to prepare various types of food and beverages with the sweeteners have been undertaken. It was found that the aspartyl dipeptide ester derivative sufficiently imparted a good intensity of sweetness, sweetness quality, etc. However, several problems were still prevalent due to an intrinsic physical property of the aspartyl dipeptide ester derivative, when it is in a powder such that it was difficult to handle. For example, such a powder has a large specific volume and most of its crystals are fine and needle-like, which provides for a dangerous work environment and an ease of losing the derivative when it is spread out.

The present inventor has also found that an aqueous solution with a high intensity of sweetness was stable and useful as a liquid sweetener composition. However, it was also observed that the solubility, the dispersibility and the stability could be improved by, for example, improving the water solubility to facilitate water solubilization by preventing the formation of coagulant (the state where the powder particles are turned into a solid mass).

As the world's population becomes increasingly focused on health, diet, etc., a non-sugar low-calorie sweetener that substitutes for sucrose is in great demand. Along these lines, there is also a need to develop ways to solve the problems that are typical of sucrose containing products, such as browning, stickiness, etc., and the suitable use of a sweetener for producing beverages, sherbets (ice block) and the like. In such production processes, various issues must be dealt with, such as, the quality of end product, the operational production efficiency, and changes in the physical property. Likewise, when prepare beverage concentrates, which will be later diluted or bottled, it is important to minimize the volume of the beverage concentrate for ease of manufacture and shipping.

Therefore, the problems that must be dealt with in this area of technology includes, among others, prevention of spreading out of the aspartyl dipeptide ester derivative; improve the solubility of the derivative for ease of dissolution; and a sweetener composition with a high intensity sweetness, which can be stored in a small place, can impart a homogeneous sweetness and be stable for a long time (high solubility and high dispersibility).

In view of the aforementioned problems, a stable sweetener composition with a high intensity sweetness containing the aspartyl dipeptide ester derivative and which can be handled easily without spreading out has been in demand.

SUMMARY OF THE INVENTION

Accordingly, one object of the present invention is to develop a solid sweetener composition in which the aspartyl dipeptide ester derivative can be homogeneously dispersed and mixed.

Another object of the present invention is to provide and obtain a liquid sweetener composition which is high in quality and facilitates process control and operational efficiency during the production and delivery.

DETAILED DESCRIPTION OF THE INVENTION

The present inventor has found that a solid sweetener composition containing at least the aspartyl dipeptide derivative and a solid filler can be obtained by a process whereby the derivative is mixed in a solution during manufacture whereby the derivative is mixed and dispersed homogeneously.

One embodiment of the present invention is a solid sweetener composition containing an aspartyl dipeptide ester derivative or a salt thereof, represented by formula (2), including formula (1); and a solid filler, whereby the composition can be produced by mixing the derivative in a solution during manufacture, whereby the derivative is mixed and dispersed homogeneously.

The sweetness intensity of the aspartyl dipeptide ester derivative in the sweetener composition is preferably more than 4,000 times that of sucrose.

The aspartyl dipeptide ester derivative in the solid sweetener composition includes salts thereof, one compound alone or mixtures thereof.

The compounds of formulas (1) and (2) are:

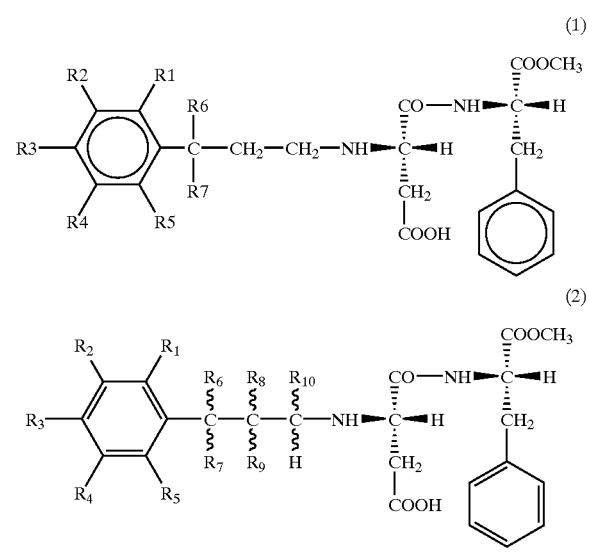

where $R_1$, $R_2$, $R_3$, $R_4$ and $R_5$ are independently a hydrogen atom, a hydroxyl group, an alkoxy group having 1 to 3 carbon atoms (methoxy, ethoxy, n-propoxy, etc.), an alkyl group having 1 to 3 carbon atoms (methyl, ethyl, n-propyl, etc.) and a hydroxyalkyloxy group having 2 or 3 carbon atoms ($O(CH_2)_2OH$, $OCH_2CH(OH)CH_3$, etc.), and where $R_1$ and $R_2$, or $R_2$ and $R_3$ may be combined together to form a methylene dioxy group ($OCH_2O$); where $R_6$, $R_7$, $R_8$, $R_9$ and $R_{10}$ are independently a hydrogen atom or an alkyl group having 1 to 3 carbon atoms (a methyl, an ethyl, an isopropyl group, etc.) and any two of $R_6$, $R_7$, $R_8$, $R_9$ and $R_{10}$, may be combined together to form an alkylene group having 1 to 5 carbon atoms ($CH_2$, $CH_2CH_2$, $CH_2CH_2CH_2$, etc.); when $R_6$ and $R_7$, or $R_8$ and $R_9$ are different substituents, or $R_{10}$ is a substituent except for a hydrogen atom, the configuration of the carbon atom to which $R_6$ and $R_7$, $R_8$ and $R_9$ or $R_{10}$ are linked, has no restriction, and may be any one of (R), (S) and (RS) or mixture thereof. The wiggly lines depicted as the bond of $R_6$ to $R_{10}$, and a hydrogen atom with a carbon atom in formula (2) means that the direction of the bond is free (is not specified).

However, where $R_6$ is a hydrogen atom or a methyl group and $R_1$, $R_2$, $R_3$, $R_4$, $R_5$, $R_7$, $R_8$, $R_9$ and $R_{10}$ are hydrogen atoms is excluded from the present invention. In addition, the derivative where $R_2$ or $R_4$ is a methoxy group, $R_3$ is a hydroxyl group, $R_{10}$ is a hydrogen atom or a methyl group, and $R_1$, $R_4$, $R_5$, $R_6$, $R_7$, $R_8$, and $R_9$ are hydrogen atoms is excluded.

The aspartyl dipeptide ester derivative used for the solid sweetener composition is preferably one where $R_8$, $R_9$ and $R_{10}$ are hydrogens. Various embodiments of the aspartyl dipeptide derivative are those compounds where: (1) $R_3$ is a hydroxyl group or a methoxy group, and $R_4$ and $R_5$ are hydrogens; (2) where $R_1$ is a hydroxyl group; (3) where $R_1$ is a hydrogen atom; (4) where $R_2$, $R_6$ and $R_7$ are hydrogens; and (5) where $R_2$ is hydrogen, a hydroxyl group or a methyl group.

Another preferred set of aspartyl dipeptide ester derivatives of the present invention are listed in the following Table 1, where all of $R_8$, $R_9$ and $R_{10}$ are hydrogens:

TABLE 1

| Derivative No. | $R_1$ | $R_2$ | $R_3$ | $R_4$ | $R_5$ | $R_6$ | $R_7$ |
|---|---|---|---|---|---|---|---|
| 1 | H | OH | $OCH_3$ | H | H | H | H |
| 2 | H | H | $OCH_3$ | H | H | H | H |
| 3 | H | OH | $OCH_3$ | H | H | $CH_3$ | $CH_3$ |
| 4 | H | $CH_3$ | OH | H | H | $CH_3$ | $CH_3$ |
| 5 | H | H | $OCH_3$ | H | H | $CH_3$ | $CH_3$ |
| 6 | H | H | OH | H | H | $CH_3$ | $CH_3$ |
| 7 | OH | H | $OCH_3$ | H | H | H | H |
| 8 | H | $CH_3$ | OH | H | H | H | H |
| 9 | OH | H | OH | H | H | H | H |

The salts of the aspartyl dipeptide ester derivatives described above include, for example, edible salts (such as hydrochloride salts), sodium salts, potassium salts, ammonium salts, calcium salts and magnesium salts, etc.

To manufacture the aspartyl dipeptide ester derivatives of the present invention Aspartame is reductively alkylated with 3-phenylpropionaldehyde derivative, cinnamaldehyde derivative or (2-phenylethyl) alkyl ketone derivative having various substituents on the phenyl group and one or two alkyl substituents on the main chain, and a reducing agent (e.g., hydrogen/palladium carbon catalyst). Alternatively, the derivative compounds can be obtained by reductively alkylating the Aspartame derivative, which has a protecting group for the carboxyl group at the β position (for example, β-o-benzyl-α-L-aspartyl-L-amino acid methyl ester), which can be obtained by ordinary peptide synthesis method (Izumiya et al., Fundamentals and experiments of peptide synthesis: Maruzen, published on 1985.1.20) with the 3-phenylpropionaldehyde derivative, cinnamaldehyde derivative or (2-phenylethyl) alkyl ketone derivative described above, and a reducing agent (e.g., $NaB(OAc)_3H$) (A. F. Abdel-Magid et al., Tetrahedron Letters, 31, 5595 (1990)), and then removing the protecting group, or by saturating the unsaturated bond with a reducing agent, if needed. An acetal or ketal derivative thereof or so on can also be used as an aldehyde or ketone component for the reductive alkylation 3-phenylpropionaldehyde derivative, cinnamaldehyde derivative or (2-phenylethyl) alkyl ketone derivative.

These derivative can be easily produced by known peptide synthesis method, or according to the production examples of derivatives 1 to 9 as described below.

The sweetening composition can include one or more aspartyl dipeptide ester compounds and/or mixed with one or more additional sweetening ingredients. The sweetener composition can also have one or more fillers. Such fillers are those ingredients that adjust the sweetness of the derivatives and include, but not limited to, sugars, sugar alcohols, oligosaccharides, polysaccharides, etc. The sweetener composition may also contain one or more bulking agents, carriers, etc. The fillers can be included in an amount so long as it does not inhibit the the object of the present invention.

The sugars include, but are not limited to, sucrose compounds, invert sugar, isomerized sugar, glucose, fructose, lactose, malt sugar, D-xylose and isomerized lactose. The sugar alcohol include, but are not limited to, maltitol (including reduced malt sugar syrup, etc.), sorbitol, mannitol, erythritol, xylitol, lactitol (including reduced lactose, etc.), paratinit, and reduced starch sugar (including hydrogenated starch syrup, etc.). The oligosaccharides include, but are not limited to, fructooligosaccharide (including neosugar, etc.), maltooligosaccharide (including linear oligosugar, etc.), isomalto-oligosaccharide (including branched oligosugar, etc.), galactooligosaccharide, soy been oligosaccharide and lactooligosaccharide, and further the polysaccharide comprises glucomannan, dietary fiber (including enzyme decomposition products of guar gum such as galactomannan Hydrolysate, etc.), non-digestible dextrin (dextrin including dietary fiber), polydextrose and starch (including dextrin, soluble starch, modified starch, etc.), etc. The fillers can be used singly or in combination.

The sucrose compounds referred to above, include, but are not limited to sugar bound syrup (including coupling sugar, glucosylsucrose, etc.), paratinose (including isomaltulose, etc.), trehalose, etc.

To make the solid sweetener composition the derivative is mixed in a solution, whereby it is preferred to completely dissolve the derivative, homogeneously, and/or an intermediate state thereof, e.g., partial dissolution and remaining partial dispersion. In another preferred embodiment, the solid sweetener composition can be obtained by homogeneously mixing the composition in a solution, and drying the solution as needed. The solvent for dissolving the aspartyl dipeptide ester compound can be any solvent, which can be used for drinking and eating and which dissolves the derivative. Such solvents include, but are not limited to water, alcohols (e.g., ethanol), polyvinyl acetate, oils and fats, etc. Methods for homogeneous mixing in a liquid solution and drying used herein are known in the art.

In another embodiment, a filler is included during the dissolving process

The solid sweetener composition containing the aspartyl dipeptide ester compound can be used as a tabletop sweetener or other type of sweetener, or in various edible products. Examples of such edible products include, but not limited to, powdered juice, powdered cocoa, powdered cola, instant coffee, black tea and so on, chocolate, chewing gum, health food, medicine, etc.

The food or beverage (e.g., a cola beverage) that is obtained using the solid sweetener composition can be used to make further products, such as a juice that can be obtained by dissolving the powdered juice in water, bread, cakes, chocolate or as a topping on such products like yogurt.

Another embodiment of the present invention is a stable liquid sweetener composition that contains the aspartyl dipeptide ester derivative with a high intensity sweetness in an edible medium, such as water, alcohol and the like. This liquid composition can be a suspension in which the aspartyl dipeptide ester derivative has been stably dissolved and stably dispersed.

The sweetness intensity of the aspartyl dipeptide ester derivative used for the liquid sweetener composition of the present invention is preferably more than 4,000 times that of sucrose.

The edible medium (water, alcohol, etc.) can include a stabilizer (bulking agent), a thickening agent, a filler, etc. These are preferably used as a medium for suspension.

At least one of the compounds contained in the group consisting of sugar, sugar alcohol, and oligosaccharide can be added as a stabilizer. As a result, a suspension having a high solubility, a high dispersibility and a high stability in terms of the derivative can be prepared.

As described above, the liquid medium is preferably water, alcohol, and a mixed solvent containing any one of water and alcohol and the like as the edible medium, also the stabilizer as described above may be included. A liquid solution can be prepared in the form of suspension, preferably a homogeneous suspension, which contains at least one of the aspartyl dipeptide ester derivatives in a high concentration than that in the solubility in the liquid medium.

The sweetener composition in the form of stable suspension can be obtained by mixing at least one of the aspartyl dipeptide ester derivatives in a higher concentration than that of the solubility of the derivative in the liquid medium. The mixing method is preferably the vacuum mixing method.

The liquid sweetener composition can be in the form of a sweetener, food, beverage, a frozen dessert, a syrup, a pharmaceutical product (medicine), oral cosmetics, such as toothpastes, among others.

There is no particular restriction to the mixing ratio of aspartyl dipeptide ester derivatives and the solid filler used in the solid sweetener composition. Preferably, the aspartyl dipeptide ester derivatives are in the amount of about 2 ppm (by weight) to about 95% (by weight) relative to the total amount of the composition, preferably in an amount of about 0.2 ppm (by weight) about to 95% (by weight).

When the solid sweetener composition is prepared, the aspartyl dipeptide ester derivative is mixed with at least with the component(s) for the composition including the filler, in a solution homogeneously.

Furthermore, the sweetener can be mixed with another sweetener ingredient(s) (another sweetener with a high intensity sweetness such as Aspartame, and the third and fourth sweetener ingredients such as sugar, sugar alcohol and the like). The compositions can also include other ingredients other than sweeteners, such as salts, e.g., sodium chloride.

When the solid sweetener composition in the present invention is used for a sweetener, various known carriers, bulking agents, etc. can be included in the composition as necessary other than the filler.

The solid sweetener composition of the present invention comprises a sweet substance and a filler, such as a sweetener, and a food comprising a sweet substance and a filler such as a fondant-like food. Moreover, the food composition can be obtained by mixing various ingredients necessary for the food other than the filler, the sweetener ingredient, etc. Ingredients imparting fruit tastes for powdered juices, flavor ingredients necessary for candy and jelly, an ingredient for tablet candy (where the outer portion is prepared separately), nutritious ingredients for nutritional supplements, pharmaceutical active ingredient(s) for pharmaceutical products, coffee ingredients for powdered coffee, dairy ingredients for powdered dairy products, dentifrice ingredients for tooth paste and tooth powder, etc. can be included in the foods as desired.

Other embodiments of the invention include, but not limited to, a tabletop sweetener composition (coating the surface of the fine crystals in powder filler), powdered cocoa, powdered cola, powdered coffee (spray dried product), instant coffee, health care foods (freeze dried product) and powdered juices (concentrated dried product), other powdered food product, granular medicine-type products, powdered flavor seasoning as a granulated product, chocolate, chewing gum, and fondant-like food.

There are no particular difficulties for producing the product in the present invention (e.g., the solid sweetener composition), and can include a mixed dispersion method using a solvent. For example, the products can be prepared as follows.

1. The composition can be produced by drying a solution of the composition in which the composition ingredients are dissolved homogeneously.
2. The composition can be included: solidifying by a method of condensation drying for Aspartame-containing sugar (refer to Japanese Patent Kokai Publication JP-A-63-146768, etc.), spray drying for the composition for imparting sweetness (refer to Japanese Patent Kokai Publication JP-A-58-20588, etc/), freeze drying for instant coffee (refer to Japanese Patent Kokai Publication JP-A-59-45849, etc.), extrusion granulation for low-calorie sweetener (refer to Japanese Patent Kokai Publication JP-A-1-206969, etc.), and absorption to form solid sweeteners (refer to Japanese Patent Kokai Publication JP-A-58-36368, etc.).

A suitable solvent to be used, include but are not limited to, any one of water, alcohol such as ethanol, and a homogeneously mixed solvent comprising at least any one of the both, is preferable.

3. The solution of the aspartyl dipeptide ester derivative(s) is coated on the surface of the filler homogeneously, for example, as described for the production of a composition containing Erythritol (refer to Japanese Patent Kokai Publication JP-A-4-335870, etc.).
4. The solvent in the solution, e.g., water, alcohol such as ethanol or a mixed solvent of the two, can be spread by spraying on the surface of the fine crystals of the powder as described, for example in Japanese Patent Kokai Publication JP-A-1-95741, etc.

Other uses of the solid sweetener composition in food and beverages, which are in need of a sweet taste include, for example, a fruit juice beverage, cola beverage, a frozen dessert, an ice cream, an ice lolly, a bread, a cake and so on, a sanitary product, cosmetics (including a oral composition such a tooth paste and powder), a medicine, a product for an animal other than human, etc.

The solid sweetener is homogeneously dispersed or mixed with the components of the food and beverage, for example, in making a juice the solid sweetener is dissolved in the water that will serve as the dissolving medium for a powdered juice product.

In another embodiment of the present invention, a liquid sweetener composition is provided. Such liquid sweetener compositions contain the aspartyl dipeptide ester derivatives represented by formula (2), particularly general formula (1), and more particularly the aforementioned 9 derivatives (referred to as "derivative 1" to "derivative 9"). While the liquid sweetener composition is explained primarily on these derivatives, the liquid sweetener composition of the present invention is not limited to the use of these derivatives.

These aspartyl dipeptide ester derivatives are prepared as described above.

The liquid sweetener composition of the present invention can include as a stabilizer a sugar, a sugar alcohol, an oligosaccharide, and mixtures therof, which are described above. Preferred for use in the liquid sweetener composition are isomerized sugar, sugar alcohol (such as sorbitol), hydrogenated starch hydrolysate and coupling sugar.

The liquid sweetener compositions of the present invention have a high intensity sweetness, which can be enriched by the addition of the sugar and the like, which can be provided at the same time as the aspartyl dipeptide ester derivatives and thereby yielding a stable liquid system. The crystals of the derivatives can be dispersed homogeneously in a liquid solution. The liquid sweetening composition of the present invention can be used for imparting sweetness in a food and/or beverage, which provides a highly practical sweetener for the raw material of beverage, desert, frozen dessert and similar products.

The aspartyl dipeptide ester derivatives generally have a low solubility in water (1 to 1000 mg/100 ml), however, the low solubility provides an intense sweetness in products containing the same. These compositions can also be a suspension containing the aspartyl dipeptide derivatives in a concentration higher than their solubility in the medium. When the viscosity of the suspension medium is low, a heterogeneous sediment may be observed, however, the sediment can be dispersed homogeneously by agitation. To keep the suspension homogeneous, it is preferable to select and use a suspension medium that has a viscosity which can maintain the stability of the suspension. For example, a solution containing a sugar can be used as a stabilizer in the edible medium (such as water), or a gum substance such as xanthan gum, guar gum, a viscosity-improving stabilizer such as a polysaccharide and a specific gravity-increasing component can be included in the compositions of the present invention. The composition can also contain components to improve solubility and dispersibility, for example viscosity-improvers, fillers or surface-active agents.

The stabilizer can be a single stabilizer or mixture of two or more stablizers thereof.

The amount of the aspartyl dipeptide ester derivative(s) in a suspension medium is preferably in an amount such that at least one part of the derivative can be maintained stably in the insoluble state. The lower limit of the amount of the aspartyl dipeptide ester derivative to produce the suspension, is an amount sufficient for providing a super saturated suspension while stored at room temperature. The upper limit of the aspartyl dipeptide ester derivative is to obtain the target intensity of sweetness. When the amount of the aspartyl dipeptide ester derivative required for the target sweetness intensity is less than the saturation amount, the solution can be used as a liquid sweetener composition.

The liquid compositions can also contain other seasoning ingredient(s) including, but not limited to sodium L-glutamate, tasty (gustatory) substances (e.g., 5'-nucleotide), sweetening substance (e.g., steviosides and saccharine), organic acid, amino acid, peptides, extracts, flavors, spices, colorants, inorganic substances like calcium and magnesium, vitamins, and lipids. The liquid sweetening composition can also contain salts, such as sodium chloride. When fats and oils are used at the same time, they can be provided as an emulsion, preferably a o/w or w/o type emulsion.

The liquid sweetener composition of the present invention can be produced by, for example, mixing one or more of the aspartyl dipeptide ester derivatives in a liquid medium to form a solution or slurry like suspension. The mixing can be also include heating and cooling the mixture as appropriate. The liquid sweetener composition can be prepared as follows:

The mixture of the aspartyl dipeptide ester derivative(s) and water, which can also include a stabilizer whereby the stabilizer and the derivatives(s) are added at the same time, or in subsequent mixing steps. Preferably, the mixture is at some point in the mixing process, preferably throughout the entire mixing process, performed under vacuum to prevent air bubbles.

The liquid sweetener composition can be in a variety of forms including, but not limited to a homogeneous solution, homogeneous dispersed solution, a paste, a fluid or semifluid of soft or hard cream-like. For example, paste-like forms, or cream-like forms are more suitable for mixing with viscous materials in a process for producing an edible product, such as a frozen dessert.

The liquid sweetener compositions of the present invention are highly stable during storage with respect to the aspartyl dipeptide ester derivative(s) whereby the aspartyl dipeptide ester derivative(s) do not decompose and remain soluble in solution for long periods of time yielding a product that is without loss of sweetness. In addition, because the stabilizer makes it possible to improve the dispersibility and solubility in water compared with the aspartyl dipeptide ester derivative alone, the sweetener composition can be used in a variety of food products or food service uses, such as beverages, sherbets, syrups and venders.

The liquid sweetener composition of the present invention can be produced as a sweetener, or directly into a form of a food or beverage, such as a frozen dessert. The liquid sweetener composition of the present invention can be used as a sweetener for various edible products including but not limited to a confectionery (a frozen dessert, a jelly, a cake, a candy), bread, chewing gum, a sanitary product, cosmetics (including an oral composition such a tooth paste and powder), a medicine and a product for an animal other than human, which are in need of an imparted sweet taste. In addition, the liquid sweetening compositions of the present invention can be used in a way that sweeteners are commonly used.

The following Examples provide an illustration of embodiments of the invention and should not be construed to limit the scope of the invention, which is set forth in the appended claims.

EXAMPLES

Example 1

Measurement of the Magnification of Sweetness Intensity

[Method for Determining the Magnification of Sweetness Intensity]

An aqueous solution was prepared by diluting derivative 2 to be PSE 10% concentration (15.5 mg/1000 ml=10/6500 g/100 ml), assuming that the intensity of sweetness of derivative 2 was 6500 times that of sucrose. Separately, aqueous sucrose solutions having sucrose concentrations of (a)6.94%, (b)8.33%, (c)10%, (d)12%, and (e)14.4% were prepared. The sensory evaluation was performed by determining which sucrose solution was closest to the solution of derivative 2 in the sweetness intensity. The result of calculation of the average of points of 20 panelists was 2.25 point.

The sweetness intensity of the solution of derivative 2 was 8.75% according to the following equation: $(10.0-8.33) \times 0.25 + 8.33 = 8.75$. Therefore, the magnification of sweetness of derivative 2 was 5600 (=8.75/0.00155) times that of sucrose. According to the same experiment, the magnification of sweetness intensity of derivative 1 was 22600 times that of sucrose. Further, the magnification of sweetness intensity of other derivatives (3 to 9) can be determined in the same manner. And the magnification of sweetness intensity in a cola beverage can be also determined by the same method compared to the control solution of cola beverage containing 10% sucrose.

Incidentally, the composition of cola beverage is as follows.

| | |
|---|---|
| Citric acid (crystal) | 0.25 g/1000 ml |
| Sodium citrate | 0.10 g/1000 ml |
| 85% Phosphoric acid | 0.3 g/1000 ml |
| Cola base | 2 ml/1000 ml |
| Cola essence | 1 ml/1000 ml |
| Sweetener (sample) | Prescribed amount |

Incidentally, as for the concentration of the references, the sucrose concentrations of previous (a) to (e) were used.

[Results]

The magnifications of sweetness intensity of the derivatives relative to that of sucrose measured as described above were shown as follows.

| Samples | In aqueous solution | In cola beverage |
|---|---|---|
| Derivative 1 | 22600 | 22600 |
| Derivative 2 | 5500 | 4900 |
| Derivative 3 | 42400 | 37000 |
| Derivative 4 | 43500 | 29600 |
| Derivative 5 | 8400 | 8000 |
| Derivative 6 | 14900 | 14000 |
| Derivative 7 | 11100 | 10600 |
| Derivative 8 | 18200 | 15800 |
| Derivative 9 | 8000 | 7500 |

Example 2

Production of Orange Juice Powder

The following ingredients were dissolved in 1000 g of water and spray dried to produce orange juice powder.

| Components | Amount (g) |
|---|---|
| Derivative 6 | 0.023 |
| Orange juice micron D-50[*1] | 31.6 |
| Anhydrous citric acid | 4.0 |
| Malic acid | 8.0 |
| Sodium citrate | 2.8 |
| Orange micron ZD-0568[*2] | 4.8 |
| Orange color base W-6540[*3] | 1.6 |
| Fruit micron CL-2068[*4] | 4.0 |
| Vitamin C | 2.0 |
| Powdered maltitol | 41.177 |
| Total | 100 |

[*1–4]Takasago Koryo, Co. Ltd.

5 g of the powder thus produced are dissolved in 150 ml of water to make an orange juice of about PSE 12% for drinking. Here, the magnification of sweetness intensity is calculated on the basis of derivative 6: 14000 times, solid component of concentrated fruit juice of orange: 1, maltitole: 0.75.

5 g of the powder produced were collected from 20 points at random, and each sample was dissolved in 150 ml of water to compare the sweetness intensity. There was no significant difference among the respective samples. The sweet taste of the solutions was equivalent to that of about PSE 12%, had been mixed and dispersed homogeneously (n=20).

On the other hand, when each 5 g of the sample was collected from 20 points of the mixture obtained only by mixing the components with the composition, and evaluated as described above, there was a significant difference in the sweetness among the respective samples, and confirmed to be heterogeneous state.

As described above, the sweetness of the sample prepared by dissolving previously and then spray drying, tasted the dispersed and preferable sweetness compared with the case of mixing powders each other. As is understood by example 1 described above, it is thought that the sweetness of the sample which is prepared by just sprinkling the powder or mixing the powders each other, is not dispersed homogeneously, because they taste a high intense sweetness and the amount of use is extremely small.

Example 3

Production of Granular Products

The sweetener composition which is easy for handling, is provided by improving the property of the aspartyl dipeptide ester derivative which is a sweetener with a high intense sweetness, and used for the present invention.

The crude powder of the derivative is generally fine, needle-like crystals, large specific volume and easy to scatter. Further, it is not dispersed or dissolved well in water. Thus, if the crude powder is dissolved in water, coagulates (insoluble aggregations) are formed, and it is difficult to dissolve in water. In addition, as the intense sweetness of the derivative is not less than 4000 times to 50000 times that of sucrose, it is necessary to measure the very small amount precisely and to mix homogeneously, when it is used as a crude powder.

However, the granular product having an improved physical property such as the solubility and dispersibility, and in which the derivative is mixed homogeneously without scattering, could be produced by the following methods.
(Ex. 1)

87 weight parts of anhydrous lactose and 8 weight parts of dextrin were mixed, and then the solution dissolved 0.2 weight parts of derivative 2 (the magnification of sweetness intensity is 5000 times) in 15 weight parts of water was added to the mixture and mixed. And the mixture was granulated by extruding, and dried to obtain the granular product. The magnification of sweetness intensity: approximately 10 times.

The results of the measurement of the physical property is as follows. Crude specific volume: 1.47 cc/g, Fine specific volume: 1.46 cc/g, Under 16 mesh to over 80 mesh:80%, Rate of dissolving: approximately 35 seconds in hot water (40° C.), approximately 26 seconds in cold water (10° C.), Dispersibility: rapid dispersion without making insoluble coagulates, Fluidity: good.
*1: As for the rate of dissolving, the distilled water was poured in the 500 ml beaker, 1 g of sample was added to the beaker with gentle mixing by magnetic stirring, and the time of dissolving was measured.

And, when the rate of dissolving of the crude derivative 2 was measured in the same way, the insoluble coagulates of crude derivative 2 were formed even in the hot water, and did not reach the complete dissolution after 5 minutes.
(Ex. 2)

90 weight parts of dextrin[*1], 5 weight parts of dextrin[*2] and 12 weight parts of the solution dissolved 0.044 weight parts of derivative 1 (the magnification of sweetness intensity is 22600 times) in water, were mixed.
*1:Amicol H (Nichiden Kagaku);
*2:Amicol No.1 (Nichiden Kagaku).

According to the above mixing, the granular product was obtained by fluid granulation. The magnification of sweetness intensity: approximately 10 times.

The rate of dissolving and so on were measured by the same methods as described in Ex. 1. As the results, Crude specific volume: 3.48 cc/g, Fine specific volume: 2.87 cc/g, Fine granule: approximately 260 μm, Rate of dissolving[*3]: approximately 15 to 20 seconds in hot water (40° C.), approximately 60 seconds in cold water (10° C.), Dispersibility: rapid dispersion without making insoluble coagulates, Fluidity: good.
*3: The method of measurement is same as described above.

Example 4

Production of Sweetener for Tabletop Use

The sweetener granule containing the following ingredients was produced by flow granulation method. At the time, derivative 1 was dissolved in the water added. The condition of the granulation is as follows. Type of coating machine:VG-1200, Feed volume:260 kg, Rotation frequency of main shaft:50 rpm, Rotation frequency of granulation shaft:900 rpm, Ratio of water added:1.0%, Mixing time:5 minutes, Temperature of hot air:80° C., Temperature of exhaust air: stop at 40° C., Particle size: ca. 700 μm, fine powder ratio (250 μm pass):2.5%.

| Components | Weight (Kg) | Composition (%) |
|---|---|---|
| Derivative 1 | 0.21 | 0.031 |
| Aspartame | 1.38 | 0.206 |
| Erythritol | 666.67 | 99.469 |
| Flavor | 1.97 | 0.294 |
| Total | 670.23 | 100 |

When 0.94 g of the sweetener produced were added to 140 ml (volume for the standard coffee cup) of coffee solution, the sweetness intensity of the coffee solution is equivalent to that of PSE 5%. The sweetness ratio of the sweetener is in derivative 1: Aspartame: Erythritol= 4:0.5:0.5. Herein the magnification of sweetness intensity of derivative 1 at PSE 4% was calculated as 18500 times, the magnification of sweetness intensity of Aspartame at PSE 0.5% was calculated as 360 times and the magnification of sweetness intensity of Erythritol at PSE 0.5% was calculated as 0.75 times.

When 5 g of the sample obtained were collected from 20 points at random, and each sample was added to 140 ml of coffee solution to compare the sweetness intensity of the coffee solution, there was no significant difference among the respective samples, and the sweetness intensity of each of the solutions was equivalent to that of PSE 5% (n=20). The mixtures of the samples had been mixed and dispersed homogeneously.

On the other hand, when each 0.94 g of the sample were collected from 20 points of the mixture obtained only by mixing the components with the composition, and evaluated by adding to the coffee solution in the same way, there was a significant difference in the sweetness among the respective samples, and confirmed to be heterogeneous state (n=20).

Example 5

Production of Fondant-Like Food

Fondant which is fine crystals of sucrose prepared by oversaturating sucrose solution and adding the impulse, is used as a decoration of cakes and sugar coat of Japanese confectionary. As the fondant is constituted by the particular shape which is enclosed by the syrup around the fine crystal of sucrose, it is confirmed that such a shape can not be formed when the sweetener composition of the aspartyl dipeptide ester derivative used in the present invention is used instead of sucrose.

On the other hand, the fondant-like foods comprising glucose, the derivatives and water at the ratio of 100:0:10 to 100:1:20 by weight, or glucose, lactose the derivatives and water at the ratio of 90:10:0:10 to 10:90:1:20 by weight, were produced.

(Ex.1) Use of Derivative 2 (as the Magnification of Sweetness Intensity is 5000 Times)

Glucose (10 g), derivative 2 (0.04 g) and water (20 g) were mixed previously, heated for 18 minutes. After the temperature of the mixture was reached at 115° C., the mixture was cooled to 60° C. and mixed to produce the fondant-like food. The magnification of sweetness intensity of this fondant-like food is approximately 2.2 times that of sucrose (when the magnification of sweetness intensity of glucose is 0.6).

(Ex.2) Use of Derivative 1 (as the Magnification of Sweetness Intensity is 22600 Times)

Glucose (50 g), lactose (50 g) and water (20 g) were mixed, heated to 115° C., and cooled to 90° C. After that, derivative 1 (0.0088 g) was added to the mixture and mixed and stirred to produce the fondant-like food. The magnification of sweetness intensity of this fondant-like food is approximately 2 times that of sucrose (when the magnification of sweetness intensity of lactose is 0.2).

Example 6

Production of Chocolates

The chocolate of the following composition was produced by the following ordinary method. With respect to derivative 8, however, it was added with flavor at the time of triturating and mixing.

| Components | Composition (g/100 ml) |
|---|---|
| Derivative 8 | 0.0015 |
| Maltitol | 40 |
| Cacaomass | 27 |
| Cacao butter | 23 |
| Powdered milk with lipid | 10 |
| Lecithin | 0.4 |
| Flavor | 0.1 |

After mixing cacaomass, cacao butter, powdered milk, maltitol and lecithin previously, the mixture was refining, couching, tempering, packing, cooling and maturing, and then the chocolate was produced. The cariostatic, low-calorie, light-taste chocolate was obtained.

Example 7

Production of Chewing Gums

The components of the following composition 1 were added to the kneader heated at 120° C. sequentially, and melt-mixed for 10 minutes. In this time, derivative 2 had been dissolved in polyvinyl acetate previously. Then, the components of the composition 2 were added to the kneader sequentially, and melt-mixed for 10 minutes in the same way. This mixture was used cooled down to room temperature, and then used as a gum base. By using this gum base, the components of the composition 3 were added to the kneader pre-heated at 75° C. sequentially, and then heating was stopped. After mixing for 12 minutes and rolling by roller, chewing gum was produced.

| Components | Mixed amounts (%) |
|---|---|
| Composition 1: | |
| Derivative 2 | 0.0003 |
| Polyvinyl acetate | 40 |
| Monoglyceride | 3.5 |
| Polybutene | 3.5 |
| Composition 2: | |
| Talc | 17 |
| Gelton | 10 |
| Wax | 6 |
| Ester gum | 20 |
| Composition 3: | |
| Gum base | 20 |
| Powder sugar | 54 |
| Syrup (Water content 20%) | 18 |
| Sorbitol | 10 |
| Flavor | 2 |
| Emulsifier | 1 |

As a comparative example, the chewing gum was produced without adding derivative 2 in the composition 1. These were stored at room temperature for overnight (maturation).

Sensory Evaluation 3 g of the chewing gum were chewed, and the change of the sweetness intensity felt in the mouse over the course of time was recorded. The sweetness intensity of the chewing gum of the comparative example disappeared after chewing for 4 minutes, and Egumi (a bitter taste in Japanese) and astringent taste were felt. However, the sweetness of the chewing gum which is mixed with the derivative 2 in the gum paste has been felt after chewing for 5 minutes, and continued effect of sweetness for 20 minutes was observed. And Egumi and astringent tastes derived from the gum paste were not felt.

Example 8

Production of the Liquid Sweetener Composition by Using the Derivative 1

1.0 weight part of derivative 1 (the magnification of sweetness intensity is 22600 times) was added to 70 weight parts of water (the solubility of the derivative 1 in water at 25° C. is 0.152 g/100 ml). After homogenizing by the homogenizer, 70 weight parts of isomerised sugar produced by Nippon Shokuhin Kakou Co. Ltd., the name of the product: "Fujikuraft" (water content 25%, the magnification of sweetness intensity: 0.75 times) were added, further homogenized and the suspension (slurry) comprising the derivative 1 was vacuum mixed by "Robokupe" (TK. SUPPLIES Co. Ltd.) with 2000 weight parts of "Fujikuraft" for 5 minutes, the sweetener composition in the form of suspension was produced. The solubilirty of the derivative 1 against "Fujikraft" at 25° C. was 0.035 g/100 ml. And, the concentartion of the derivative 1 in the sweetener composition in the form of suspension is 0.047 g/100 ml (=1/2141; as the specific gravity is 1).

As 1 ml of the sweetener composition in the form of suspension has the sweetness intensity equivalent to 11.3 of sucrose, when 0.5 ml are dropped in the 140 ml of coffee which is a standard volume of a coffee cup, the coffee having the sweetness intensity equivalent to that of 4% sucrose is obtained.

| *Calculation of the sweetness intensity | |
|---|---|
| from derivative 1 | 1 × 22600 |
| from "Fujikuraft" | (70 + 2000) × 0.75 |
| Total | 24152.5 |

Therefore, if it is 1 g, specific gravity 1, the sweetness intensity is 11.3=24152.5/2141 per 1 ml.

Although the sweetener composition in the form of suspension was poured into 20 ml scale graduated cylinder, the top of the cylinder was wrapped by the transparent film for preventing the evaporation and it was stood still at room temperature for 60 days, the precipitation of derivative 1 can not be obtained. The viscosity of the sweetener composition in the form of suspension was 410 mPa.s (centipoise: 20° C., digital viscometer DVN-B type of Tokyo Keiki Co. Ltd., rotor No.2, 30 rpm, 1 minute).

In the same way, when the suspension which was prepared by adding 1.0 weight part of derivative 1 to 70 weight parts of water and homogenizing the mixture by homogenizer, was stood still at room temperature for 7 days in the same way, all suspended substances were precipitated.

After producing the sweetener composition in the form of suspension, when the sensory evaluation was performed by comparing the 140 ml coffee which was added 0.5 ml of the sweetener composition with 140 ml coffee which was added 5.6 g of sucrose (sucrose 4%) as a reference, any significant difference was not observed in the sweetness. And, the sweetener composition in the form of suspension was poured into the sealed container and stood still at room temperature for 60 days. After that, when the sensory evaluation was performed by comparing the 140 ml coffee which was added 0.5 ml of the sweetener composition with 140 ml coffee which was added 5.6 g of sucrose as a reference in the same way, any significant difference was not observed in the sweetness, delicious coffee was obtained. From these results, it was found that the derivative 1 was not decomposed and it was stable.

When 50 g of the suspension of the derivative (derivative content 0.0234 g) were added to 500 ml of water (25° C.) with stirring (200 rpm), and the time required to dissolve completely was measured, it took 50 seconds. When 0.0234 g of the powder of the derivative 1, as a reference product, were added to 500 ml of water (25° C.) with stirring (200 rpm) in the same way, and the time required to dissolve completely was measured, it took not less than 3 minutes.

From the results of above Example 8, it was understood that the sweetener composition of the present invention was obtained stably, and it was also confirmed that the stability was increased extremely by adding the stabilizer such as isomerised sugar, compared with the case of water alone.

Example 9

Production of the Liquid Sweetener Composition by Using Derivative 2

The following suspension medium was produced.

| Components | Weights (g) |
|---|---|
| D-sorbitol (70% aqueous solution) | 303 |
| Degassed distilled water | 45 |
| Sodium benzoate | 0.62 |
| Sodium carboxymethyl cellulose | 0.03 |
| Polysorbate 80 | 1.35 |
| Total | 350 |

In the components constituting the above composition, D-sorbitol which is used as a stabilizer for high solubility and high dispersibility, was expected both to improve the taste quality and to form the viscosity (a filler), and the degassed distilled water was used to remove the influence for the rate of precipitation of the derivative 2 by dissolved gases and dissolved ions. And, Sodium benzoate was used as a fungicide, Polysorbate 80 was used as a surfactant for improving the solubility of the derivative 2. Sodium carboxymethyl cellulose was used as a stabilizer for dispersion, particularly, a stabilizer for increasing the viscosity. The viscosity of this suspension was approximately 56 mPa.s (centipoise, measuring conditions: 20° C., rotor No.2, 30 rpm, 1 minute, digital viscometer DVN-B type of Tokyo Keiki Co. Ltd.).

58.3 g of the above suspension medium (dispersion medium) were fractionated into a 100 ml-scale beaker, 0.160 g of the powder of derivative 2 (the particle size [median diameter] was evened up to approximately 12 μm) were measured and added into the beaker for stirring by using a stirrer (at 20° C., for 30 minutes). After that, the suspension was transferred to the 50 ml scale Meβzylinder from the beaker, the Meβzylinder was stood still, and the volume of the supernatant was measured at regular intervals of time (20° C.). The solubility of the derivative 2 in water is 0.009 g/100 ml (25° C.). As a reference, Aspartame was used in place of derivative 2.

| Sample No. | Sweetener | Magnification of sweetness intensity (vs. sucrose) | Amount of use (g) | vs. dispersion medium 58.3 g (%) |
|---|---|---|---|---|
| 1 | Derivative 2 | 5000 | 0.160 | 0.27 |
| 2 (Comparable example) | Aspartame | 200 | 4 | 6.86 |

The volumes of the supernatant (ml) at regular intervals of time are shown as follows.

| Sample No. | 0 hour | 24 hours | 48 hours | 72 hours | 3 months |
|---|---|---|---|---|---|
| 1 | 0 | 0 | 0 | 0 | 0 |
| 2 (Comparable example) | 0 | 9 | 18 | 25 | Precipitate all |

As a result, with respect to the product of the present invention, the precipitation of the supernatant was not observed. By using the derivative 2 in the form of suspension, the sweetener composition with a high intense sweetness in the form of suspension, which is more stable (without precipitation) and in which the sweetness is dispersed homogeneously, can be provided. As the stable sweetener composition in the form of suspension can be provided even under the low viscosity (for example, not more than 100 mPa s), the tabletop sweetener or the portable sweetener which is highly fluid and convenient when one or two drops of the sweetener is added in coffee and black tea. For example, when 0.5 g of the obtained sweetener composition in the form of suspension are added to 140 ml of coffee, the sweetness intensity equivalent to approximately 5% sucrose can be obtained. And, it is suitable for the use in the vending machine. Further, it is understood that it can be used for sprinkling on the sherbet as a sweetener, and imparting the sweetness after cooking.

When the sweetener composition with the same intensity of sweetness by using derivative 1 is wanted to produce, 0.035 g of derivative 1 (4/22600) may be added to 58.3 g of the above suspension medium (the dispersion medium). In this case, derivative 1 is dissolved in the form of solution. When the sweetener composition is wanted to use in the form of solution considering the concentration for the respective object, it is not necessary to make any suspension. When 0.5 g of the obtained the sweetener composition in the form of suspension are added to 140 ml of coffee, the sweetness intensity equivalent to approximately 5% sucrose can be obtained. The solubility of derivative 1 in water is 0.152 g/100 ml (25° C.).

Hereinafter, Production Examples of the aspartyl dipeptide ester derivatives which are used for the present invention are shown.

Production Example 1

Production of Derivative 1

Synthesis of N-[N-[3-(3-hydroxy-4-methoxyphenyl) propyl]-L-α-aspartyl]-L-phenylalanine 1-methyl ester To 485 mg (1.0 mmol) of N-t-butoxycarbonyl-β-o-benzyl-α-L-aspartyl-L-phenylalanine methyl ester, 5 ml of a 4N-HCl/dioxane solution were added and stirred at room temperature for one hour. The reaction solution was concentrated under reduced pressure. To the residue were added 30 ml of a 5%-aqueous solution of sodium hydrogen carbonate and extraction was made twice with 30 ml of ethyl acetate. An organic layer was washed with a saturated saline water and dried over anhydrous magnesium sulfate. Magnesium sulfate was filtered off and the liquid filtrate was concentrated under reduced pressure to yield 385 mg of β-o-benzyl-α-L-aspartyl-L-phenylalanine methyl ester, as a viscous oily substance.

385 mg (1.0 mmol) of the above β-o-benzyl-α-L-aspartyl-L-phenylalanine methyl ester were dissolved in 15 ml of tetrahydrofuran (THF) to yield a solution which was maintained at 0° C. To this solution were added 268 mg (1.0 mmol) of 3-benzyloxy-4-methoxycinnamaldehyde, 0.060 ml (1.0 mmol) of acetic acid and 318 mg (1.5 mmol) of NaB(OAc)$_3$H and stirred for one hour at 0° C. and overnight at room temperature. To the reaction solution were added 50 ml of a saturated aqueous solution of sodium hydrogen carbonate and extraction was made twice with 30 ml of ethyl acetate. An organic layer was washed with a saturated saline water and dried over anhydrous magnesium sulfate. Magnesium sulfate was filtered off and the liquid filtrate was concentrated under reduced pressure. The residue was purified with preparative thin layer chromatography (PTLC) to yield 523 mg (0.82 mmol) of N-[N-[3-(3-benzyloxy-4-methoxyphenyl) propenyl]-β-o-benzyl-L-α-aspartyl]-L-phenylalanine 1-methyl ester as a viscous oily substance. To above 523 mg (0.82 mmol) of N-[N-[3-(3-benzyloxy-4-methoxyphenyl) propenyl]-β-o-benzyl-L-α-aspartyl]-L-phenylalanine 1-methyl ester were dissolved in a mixed solvent of 30 ml of methanol and 1 ml of water, and 200 mg of 10% palladium carbon (containing 50% of water) were added thereto. The resulting mixture was reduced at room temperature for three hours under a hydrogen atmosphere. The catalyst was filtered off and the filtrate was concentrated under reduced pressure. The residue was purified with PTLC to remove an odor adsorbed to yield 228 mg (0.48 mmol) of N-[N-[3-(3-hydroxy-4-methoxyphenyl) propyl]-L-α-aspartyl]-L-phenylalanine 1-methyl ester as a solid substance.

$^1$HNMR (DMSO-d$_6$) δ:1.50–1.60 (m, 2H), 2.15–2.40 (m,6H), 2.87–2.97 (dd, 1H), 3.05–3.13 (dd, 1H), 3.37–3.43 (m, 1H), 3.62 (s, 3H), 3.71 (s, 3H), 4.50–4.60 (m, 1H), 6.52 (d, 1H), 6.60 (s, 1H), 6.79 (d, 1H), 7.18–7.30 (m, 5H), 8.52 (d, 1H), 8.80 (brs, 1H).

ESI(Electrospray Ionization)-MS 459.2 (MH$^+$).

Production Example 2

Production of Derivative 2

Synthesis of N-[N-[3-(4-methoxyphenyl) propyl]-L-α-aspartyl]-L-phenylalanine 1-methyl ester 405 mg (2.5 mmol) of 4-methoxycinnamaldehyde, 735 mg (2.5 mmol) of aspartame and 350 mg of 10% palladium carbon (containing 50% of water) were added to a mixed solvent of 15 ml of methanol and 5 ml of water, stirred overnight at room temperature under a hydrogen atmosphere. The catalyst was filtered off and the filtrate was concentrated under reduced pressure. To the residue were added 30 ml of ethyl acetate, stirred for awhile and then insoluble materials ware collected by filtration. After washing the collected insoluble materials with a little amount of ethyl acetate, 50 ml of a mixed solvent of ethyl acetate and methanol (5:2) were added to them and they were stirred for a while. Insoluble materials were removed by filtration, and the filtrate was concentrated until all the residue became the solid. This was dried under reduced pressure, and recrystalized in the mixed solvent of methanol and water, to obtain N-[N-[3-(4-methoxyphenyl) propyl]-L-α-aspartyl]-L-phenylalanine 1-methyl ester as a solid with a total yield of 43.4%.

Production Example 3

Production of Derivative 3

Synthesis of N-[N-[3-(3-hydroxy-4-methoxyphenyl)-3-methylbutyl]-L-α-aspartyl]-L-phenylalanine 1-methyl ester To 703 mg (1.45 mmol) of N-t-butoxycarbonyl-β-o-benzyl-(α-L-aspartyl-L-phenylalanine methyl ester, 10 ml of a 4N-HCl/dioxane solution were added and stirred at room temperature for one hour. The reaction solution was concentrated under reduced pressure. To the residue were added 50 ml of a 5%-aqueous solution of sodium hydrogen carbonate and extraction was made twice with 50 ml of ethyl acetate. An organic layer was washed with a saturated saline water and dried over anhydrous magnesium sulfate. Magnesium sulfate was filtered off and the liquid filtrate was concentrated under reduced pressure to yield 557 mg (1.45 mmo) of β-o-benzyl-α-L-aspartyl-L-phenylalanine methyl ester, as a viscous oily substance.

557 mg (1.45 mmol) of the above β-o-benzyl-α-L-aspartyl-L-phenylalanine methyl ester were dissolved in 15 ml of tetrahydrofuran (THF) to yield a solution which was maintained at 0° C. To this solution were added 432 mg (1.45 mmol) of 3-(3-benzyloxy-4-methoxyphenyl)-3-methylbutyl aldehyde, 0.083 ml (1.45 mmol) of acetic acid and 462 mg (2.18 mmol) of NaB(OAc)$_3$H and stirred for one hour at 0° C. and overnight at room temperature. To the reaction solution were added 50 ml of a saturated aqueous solution of sodium hydrogen carbonate and extraction was made twice with 50 ml of ethyl acetate. An organic layer was washed with a saturated saline water and dried over anhydrous magnesium sulfate. Magnesium sulfate was filtered off and the liquid filtrate was concentrated under reduced pressure. The residue was purified with preparative thin layer chromatography (PTLC) to yield 832 mg (1.25 mmol) of N-[N-[3-(3-benzyloxy-4-methoxyphenyl)-3-methylbutyl]-β-o-benzyl-L-α-aspartyl]-L-phenylalanine 1-methyl ester as a viscous oily substance. To above 832 mg (1.25 mmol) of N-[N-[3-(3-benzyloxy-4-methoxyphenyl)-3-methylbutyl]-β-o-benzyl-L-α-aspartyl]-L-phenylalanine 1-methyl ester were dissolved in a mixed solvent of 25 ml of methanol and 2 ml of water, and 350 mg of 10% palladium carbon (containing 50% of water) were added thereto. The resulting mixture was reduced at room temperature for three hours under a hydrogen atmosphere. The catalyst was filtered off and the filtrate was concentrated under reduced pressure. The residue was purified with PTLC to remove an odor adsorbed to yield 400 mg (0.82 mmol) of N-[N-[3-(3-hydroxy-4-methoxyphenyl)-3-methylbutyl]-L-α-aspartyl]-L-phenylalanine 1-methyl ester as a solid substance.

$^1$HNMR (DMSO-d$_6$) δ:1.14 (s,6H), 1.54–1.68(m,2H), 2.04–2.22 (m,3H), 2.24–2.34 (dd, 1H), 2.84–2.94 (dd, 1H), 3.00–3.08 (dd, 1H), 3.31–3.36 (m, 1H), 3.59 (s, 3H), 3.71 (s,3H), 4.46–4.55 (m, 1H), 6.60–6.65 (dd, 1H), 6.73 (s, 1H), 6.80 (d, 1H), 7.10–7.28 (m,5H), 8.45 (d, 1H), 8.75 (brs, 1H).

ESI-MS 487.3 (MH$^+$)

Production Example 4

Production of Derivative 4

Synthesis of N-[N-[3-(3-methyl-4-hydroxyphenyl)-3-methylbutyl]-L-α-aspartyl]-L-phenyl alanine 1-methyl ester N-[N-[3-(3-methyl-4-hydroxyphenyl)-3-methylbutyl]-L-α-aspartyl]-L-phenylalanine 1-methyl ester was obtained as a solid substance, with a total yield of 63.2%, in the same way as in Production Example 3, except using 3-(3-methyl-4-benzyloxyphenyl)-3-methylbutyl aldehyde in place of 3-(3-benzyloxy-4-methoxyphenyl)-3-methylbutyl aldehyde.

$^1$HNMR (DMSO-d$_6$) δ:1.14 (s,6H), 1.59–1.68 (m,2H), 2.09 (s,3H), 2.09–2.18 (m,3H), 2.25 (dd,1H), 2.90 (dd,1H), 3.02 (dd,1H), 3.30–3.36 (m,1H), 3.59 (s,3H), 4.46–4.54 (m,1H), 6.68 (d,1H), 6.88 (dd,1H), 6.96 (s,1H), 6.14–6.73 (m,5H), 8.46 (d,1H), 9.01 (brs, 1H).

ESI-MS 471.4 (MH$^+$)

(Production Example 5

Production of Derivative 5

Synthesis of N-[N-[3-(4-methoxyphenyl)-3-methylbutyl]-L-α-aspartyl]-L-phenylalanine 1-methyl ester N-[N-[3-(4-methoxyphenyl)-3-methylbutyl]-L-α-aspartyl]-L-phenylalanine 1-methyl ester was obtained as a solid substance, with a total yield of 72.2%, in the same way as in Production Example 3, except using 3-(4-methoxyphenyl)-3-methylbutyl aldehyde in place of 3-(3-benzyloxy-4-methoxyphenyl)-3-methylbutyl aldehyde.

$^1$HNMR (DMSO-d$_6$) δ:1.17 (s, 6H), 1.62–1.72 (m,2H), 2.04–2.20 (m, 3H), 2.24–2.34 (dd, 1H), 2.84–2.94 (dd, 1H), 2.95–3.07 (dd,1H), 3.30–3.35 (m, 1H), 3.51 (s, 3H), 3.70 (s,3H), 4.46–4.54 (m,1H), 6.83 (d,2H), 7.14–7.28 (m, 7H), 8.43 (d, 1H).

ESI-MS 471.3 (MH$^+$)

(Production Example 6

Production of Derivative 6

Synthesis of N-[N-[3-(4-hydroxyphenyl)-3-methylbutyl]-L-α-aspartyl]-L-phenylalanine 1-methyl ester N-[N-[3-(4-hydroxyphenyl)-3-methylbutyl]-L-α-aspartyl]-L-phenylalanine 1-methyl ester was obtained as a solid substance, with a total yield of 64.5%, in the same way as in Production Example 3, except using 3-(4-benzyloxyphenyl)-3-methylbutyl aldehyde in place of 3-(3-benzyloxy-4-methoxyphenyl)-3-methylbutyl aldehyde.

$^1$HNMR (DMSO-d$_6$) δ:1.15 (s, 6H), 1.58–1.72 (m,2H), 2.04–2.20 (m, 3H), 2.24–2.34 (dd, 1H), 2.85–2.94 (dd, 1H), 3.00–3.08 (dd,1H), 3.30–3.36 (m, 1H), 3.59 (s, 3H), 4.46–4.55 (m,1H), 6.67 (d,2H), 7.07 (d, 2H), 7.10–7.27 (m, 5H), 8.44 (d, 1H), 9.15 (brs,1H).

ESI-MS 457.3 (MH$^+$)

Production Example 7

Production of Derivative 7

Synthesis of N-[N-[3-(2-hydroxy-4-methoxyphenyl) propyl]-L-α-aspartyl]-L-phenylalanine 1-methyl ester N-[N-[3-(2-hydroxy-4-methoxyphenyl) propyl]-L-α-aspartyl]-L-phenylalanine 1-methyl ester was obtained as a solid substance, with a total yield of 54.4%, in the same way as in Production Example 1, except using 2-benzyloxy-4-methoxycinnamaldehyde in place of 3-benzyloxy-4-methoxycinnamaldehyde.

$^1$HNMR (DMSO-d$_6$) δ: 1.52–1.57 (m,2H), 2.20–2.31 (m, 2H), 2.26–2.41 (m, 4H), 2.88–3.11 (m, 2H), 3.41–3.43 (m, 1H), 3.62 (s, 3H), 3.65 (s, 3H), 4.53–4.59 (m,1H), 6.28–6.36 (m, 2H), 6.88–6.90 (d,1H), 7.19–7.29 (m, 5H), 8.55 (d, 1H).

ESI-MS 459.3 (MH$^+$)

Production Example 8

Production of Derivative 8

Synthesis of N-[N-[3-(3-methyl-4-hydroxyphenyl) propyl]-L-α-aspartyl]-L-phenylalanine 1-methyl ester N-[N-[3-(3-methyl-4-hydroxyphenyl) propyl]-L-α-aspartyl]-L-phenylalanine 1-methyl ester was obtained as a solid substance, with a total yield of 32.2%, in the same way as in Production Example 1, except using 3-methyl-4-benzyloxycinnamaldehyde in place of 3-benzyloxy-4-methoxycinnamaldehyde.

$^1$HNMR (DMSO-d$_6$) δ:1.50–1.58 (m,2H), 2.08 (s, 3H), 2.09–2.30 (m, 2H), 2.26–2.38 (m, 4H), 2.89–3.09 (m, 2H), 3.35–3.42 (m, 1H), 3.62 (s, 3H), 4.54–4.59 (m,1H), 6.65–6.83 (m, 3H), 7.19–7.28 (m, 5H), 8.52 (d, 1H), 9.04 (brs, 1H).

ESI-MS 443.4 (MH$^+$)

Production Example 9

Production of Derivative 9

Synthesis of N-[N-[3-(2,4-dihydroxyphenyl) propyl]-L-α-aspartyl]-L-phenylalanine 1-methyl ester N-[N-[3-(2,4-dihydroxyphenyl) propyl]-L-α-aspartyl]-L-phenylalanine 1-methyl ester was obtained as a solid substance, with a total yield of 42.6%, in the same way as in Production Example 1, except using 345 mg (1.0 mmol) of 3-(2,4-dibenzyloxyphenyl)-2-propenylaldehyde in place of 268 mg (1.0 mmol) of 3-benzyloxy-4-methoxycinnamaldehyde.
ESI-MS 445.3 (MH$^+$)

Effect of the Invention

According to the present invention, a solid sweetener composition (including the form of solid food) which is produced by mixing homogeneously an aspartyl dipeptide ester derivative (one kind or more; which may be in the salt form) contained in the above general formula (2), particularly (1), with a filler (including a bulking agent and a carrier and so on) in the form of solution (if necessary, including the drying process), wherein the sweetness of the derivative is dispersed and mixed homogeneously, can be provided.

By the present invention, by mixing homogeneously with the various fillers used for the solid sweetener composition of the present invention, a solid sweetener composition with a high intense sweetness having a homogeneous taste characteristics which can not be obtained by the single use of one kind or more of the derivatives represented by the above general formula (2), particularly (1), can be provided. It can be used as a solid sweetener and solid food (powdered juice and so on), and as a sweetness imparting agent for the product such as food and beverage which is required the homogeneous sweetness.

Furthermore, according to the present invention, the stable solution or the suspension (a liquid sweetener composition of the present invention) as a sweetener composition, which comprises one kind or more of the aspartyl dipeptide ester derivative (which may be in the salt form) represented by the above general formula (2), particularly (1), in the edible medium such as water, can be obtained.

This liquid sweetener composition is superior in solubility, or particularly in dispersibility, and can be stored in a small place for a long time, having a superior in operation, without problems of scattering and so on. It can be used simply as a sweetener and food and beverage, or as a sweetness imparting agent for food and beverage and so on. For example, although it exerts the superiority as a sherbet, a syrup and a sweetener for the vending machine, it can be applicable widely without any limitation of these products, for various products in need of imparting sweetness.

What is claimed is:

1. A process of making a composition of an aspartyl dipeptide ester compound, comprising mixing an aspartyl dipeptide ester compound or salts thereof represented by formula (1) and a solid filler in a solution:

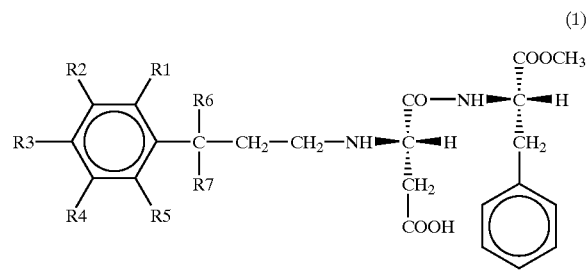

(1)

wherein R$_3$ is selected from the group consisting of of a hydrogen atom, a hydroxyl group, a methoxy group and a methyl group, wherein
a) when R$_3$ is a hydroxyl group, R$_1$ and R$_5$ are independently selected from the group consisting of a hydrogen atom, a hydroxyl group, a methoxy group and a methyl group, R$_2$ and R$_4$ are independently selected from the group consisting of a hydrogen atom, a hydroxyl group, and a methyl group, and R$_6$ and R$_7$ are independently a hydrogen atom or a methyl group;
b) when R$_3$ is a methoxy group, R$_1$, R$_2$, R$_4$, and R$_5$ are independently selected from the group consisting of a hydrogen atom, a hydroxyl group, a methoxy group and a methyl group, and R$_6$, and R$_7$ are independently a hydrogen atom or a methyl group; and
c) when R$_3$ is a hydrogen atom or a methyl group, R$_1$, R$_2$, R$_4$, and R$_5$ are independently selected from the group consisting of a hydrogen atom, a hydroxyl group, a methoxy group and a methyl group, and R$_6$ and R$_7$ are independently a hydrogen atom or a methyl group so long as at least one of R$_1$, R$_2$, R$_4$, and R$_5$ is a hydroxyl group or a methoxy group;
and when R$_6$ and R$_7$ are different substituents the carbon atom to which these substituents are linked is in the (R), (S) or (RS) configuration,
wherein said composition is in a form selected from the group consisting of a liquid composition, a solid composition, and a paste-like composition.

2. The process as defined in claim 1, wherein the sweetness intensity of the aspartyl dipeptide ester compound is more than 4,000 times that of sucrose.

3. The process as defined in claim 2, wherein R$_3$ is a hydroxyl group or a methoxy group; and R$_4$ and R$_5$ are hydrogens.

4. The process as defined in claim 3, wherein R$_1$ is a hydroxyl group.

5. The process as defined in claim 3, wherein R$_1$ is a hydrogen atom.

6. The process as defined in claim 4, wherein R$_2$, R$_6$ and R$_7$ are hydrogens.

7. The process as defined in claim 5, wherein R$_2$ is a hydrogen atom, a hydroxyl group or a methyl group.

8. The process as defined in claim 1, wherein the aspartyl dipeptide ester compound is selected from the group consisting of: (1) a compound wherein R$_1$, R$_4$, R$_5$, R$_6$, and R$_7$ are hydrogen, R$_2$ is OH, R$_3$ is OCH$_3$; (2) a compound wherein R$_1$, R$_2$, R$_4$, R$_5$, R$_6$, and R$_7$ are hydrogen, R$_3$ is OCH$_3$; (3) a compound wherein R$_1$, R$_4$, and R$_5$, are hydrogen, R$_2$ is OH, R$_3$ is OCH$_3$, R$_6$ and R$_7$ are CH$_3$; (4) a compound wherein R$_1$, R$_4$, and R$_5$ are hydrogen, R$_2$ is CH$_3$, R$_3$ is OH, R$_6$ and R$_7$ are CH$_3$; (5) a compound wherein R$_1$, R$_2$, R$_4$, and R$_5$ are hydrogen, R$_3$ is a OCH$_3$, R$_6$ and R$_7$ is CH$_3$; (6) a compound wherein R$_1$, R$_2$, R$_4$, and R$_5$ are hydrogen, R$_3$ is OH, R$_6$ and R$_7$ is CH$_3$ ; (7) a compound wherein R$_1$ is OH, R$_2$, R$_4$, R$_5$, R$_6$ and R$_7$ are hydrogen, R$_3$ is a OCH$_3$; (8) a compound wherein R$_1$, R$_4$, R$_5$, R$_6$, and R$_7$ are hydrogen, R$_2$ is a CH$_3$, R$_3$ is OH; and (9) a compound wherein R$_1$ and R$_3$ are OH, R$_2$, R$_4$, R$_5$, R$_6$, and R$_7$ are hydrogen.

9. The process as defined in claim 1, wherein the solid filler is at least one of the compound selected from the group consisting of sugar, sugar alcohol, oligosaccharide and polysaccharide.

10. The process as defined in claim 9, wherein the sugar is a sucrose compound, invert sugar, isomerized sugar, glucose, fructose, lactose, malt sugar, D-xylose or isomerized lactose.

11. The process as defined in claim 9, wherein the sugar alcohol is maltitol, sorbitol, mannitol, erythritol, xylitol, lactitol, palatinit, or reduced starch sugar.

12. The process as defined in claim 9, wherein the oligosaccharide is fructooligosaccharide, maltooligosaccharide, isomalto-oligosaccharide, galactooligosaccharide, soy been oligosaccharide, or lactooligosaccharide.

13. The process as defined in claim 9, wherein the polysaccharide is glucomannan, dietary fiber, an enzyme decomposition product of guar gum, non-digestible dextrin, polydextrin, starch, dextrin, soluble starch, or modified starch.

14. The process as defined in claim 1, wherein the aspartyl dipeptide ester compound is in an amount of from 2 ppm to 95% by weight of the composition.

15. The process as defined in claim 1, further comprising drying the solution.

16. The process as defined in claim 1, further comprising solidifying the composition.

17. The process as defined in claim 16, wherein the solidifying comprise a method selected from the group consisting of condensation drying, spray drying, freeze drying, extrusion granulation and absorption to forming sugar.

18. The process as defined in claim 1, wherein solution comprise a solvent of water, alcohol, or a mixture of water and alcohol.

19. The process as defined in claim 1, wherein the mixing comprises homogeneously coating the filler with a solution of the aspartyl dipeptide ester compound.

20. A composition produced by a process, comprising mixing an aspartyl dipeptide ester compond represented by formula (1) or a salt thereof; and a solid filler in a solution:

(1)

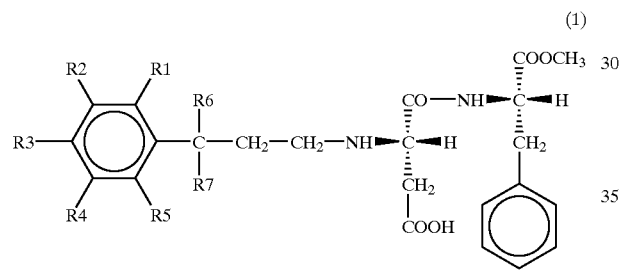

wherein $R_3$ is selected from the group consisting of a hydrogen atom, a hydroxyl group, a methoxy group and a methyl group, wherein
  d) when $R_3$ is a hydroxyl group, $R_1$ and $R_5$ are independently selected from the group consisting of a hydrogen atom, a hydroxyl group, a methoxy group and a methyl group, $R_2$ and $R_4$ are independently selected from the group consisting of a hydrogen atom, a hydroxyl group, and a methyl group, and $R_6$ and $R_7$ are independently a hydrogen atom or a methyl group;
  e) when $R_3$ is a methoxy group, $R_1$, $R_2$, $R_4$, and $R_5$ are independently selected from the group consisting of a hydrogen atom, a hydroxyl group, a methoxy group and a methyl group, and $R_6$ and $R_7$ are independently a hydrogen atom or a methyl group; and
  f) when $R_3$ is a hydrogen atom or a methyl group, $R_1$, $R_2$, $R_4$, and $R_5$ are independently selected from the group consisting of a hydrogen atom, a hydroxyl group, a methoxy group and a methyl group, and $R_6$ and $R_7$ are independently a hydrogen atom or a methyl group so long as at least one of $R_1$, $R_2$, $R_4$, and $R_5$ is a hydroxyl group or a methoxy group;
  and when $R_6$ and $R_7$ are different substituents, the carbon atom to which these substituents are linked is in the (R), (S) or (RS) configuration,
  wherein said composition is in a form selected from the group consisting of a liquid composition, a solid composition, and a paste-like composition.

21. A sweetened edible product, comprising the composition as defined in claim 20.

22. The sweetened edible product as defined in claim 21, which is selected from the group consisting of a sweetener, juice, coffee, cocoa, powdered cola, black tea, health care food, chewing gum, chocolate, medicine and solid tooth paste.

23. A process of producing liquid composition, comprising dissolving in a edible liquid medium at least one aspartyl dipeptide ester compound or salt thereof represented by formula (I):

(1)

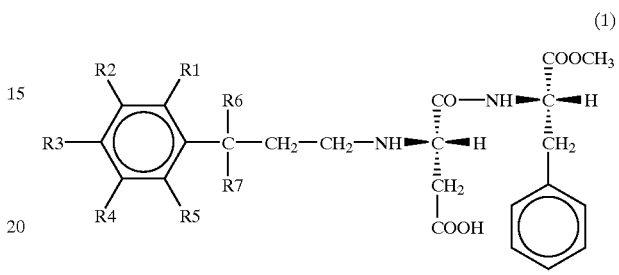

wherein $R_3$ is selected from the group consisting of a hydrogen atom, a hydroxyl group, a methoxy group and a methyl group, wherein
  g) when $R_3$ is a hydroxyl group, $R_1$ and $R_5$ are independently selected from the group consisting of a hydrogen atom, a hydroxyl group, a methoxy group and a methyl group, $R_2$ and $R_4$ are independently selected from the group consisting of a hydrogen atom, a hydroxyl group, and a methyl group, and $R_6$ and $R_7$ are independently a hydrogen atom or a methyl group;
  h) when $R_3$ is a methoxy group, $R_1$, $R_2$, $R_4$, and $R_5$ are independently selected from the group consisting of a hydrogen atom, a hydroxyl group, a methoxy group and a methyl group, and $R_6$ and $R_7$ are independently a hydrogen atom or a methyl group; and
  i) when $R_3$ is a hydrogen atom or a methyl group, $R_1$, $R_2$, $R_4$, and $R_5$ are independently selected from the group consisting of a hydrogen atom, a hydroxyl group, a methoxy group and a methyl group, and $R_6$ and $R_7$ are independently a hydrogen atom or a methyl group so long as at least one of $R_1$, $R_2$, $R_4$, and $R_5$ is a hydroxyl group or a methoxy group;
  and when $R_6$ and $R_7$ are different substituents the carbon atom to which these substituents are linked is in the (R), (S) or (RS) configuration.

24. The process as defined in claim 23, wherein the sweetness intensity of the aspartyl dipeptide ester compound is more than 4,000 times that of sucrose.

25. The process as defined in claim 23, wherein $R_3$ is a hydroxyl group or a methoxy group; and $R_4$ and $R_5$ are hydrogens.

26. The process as defined in claim 25, wherein $R_1$ is a hydroxyl group.

27. The process as defined in claim 26, wherein $R_1$ is hydrogen.

28. The process as defined in claim 27, wherein $R_2$, $R_6$, and $R_7$ are hydrogens.

29. The process as defined in claim 28 wherein $R_2$ is hydrogen, a hydroxyl group or a methyl group.

30. The process as defined in claim 23, wherein the aspartyl dipeptide ester compound is selected from the group consisting of: (1) a compound wherein $R_1$, $R_4$, $R_5$, $R_6$, and $R^7$ are hydrogen, $R_2$ is OH, $R_3$ is $OCH_3$; (2) a compound wherein $R_1$, $R_2$, $R_4$, $R_5$, $R_6$, and $R_7$ are hydrogen, $R_3$ is OCH$_3$; (3) a compound wherein R$_1$, R$_4$, and R$_5$, are hydrogen, R$_2$ is OH, R$_3$ is OCH$_3$, R$_6$ and R$_7$ are CH$_3$; (4) a compound wherein R$_1$, R$_4$, and R$_5$ are hydrogen, R$_2$ is CH$_3$, R$_3$ is OH, R$_6$ and R$_7$ are CH$_3$; (5) a compound wherein R$_1$, R$_2$, R$_4$, and R$_5$ are hydrogen, R$_3$ is a OCH$_3$, R$_6$ and R$_7$ is CH$_3$; (6) a compound wherein R$_1$, R$_2$, R$_4$, and R$_5$ are hydrogen, R$_3$ is OH, R$_6$ and R$_7$ is CH$_3$; (7) a compound wherein R$_1$ is OH, R$_2$, R$_4$, R$_5$, R$_6$ and R$_7$ are hydrogen, R$_3$ is a OCH$_3$; (8) a compound wherein R$_1$, R$_4$, R$_5$, R$_6$ and R$_7$ are hydrogen, R$_2$ is a CH$_3$, R$_3$ is OH; and (9) a compound wherein R$_1$ and R$_3$ are OH, R$_2$, R$_4$, R$_5$, R$_6$ and R$_7$ are hydrogen.

31. The process as defined in claim 23, further comprising mixing at least one of the compound selected from the group consisting of sugar, sugar alcohol, and oligosaccharide.

32. The process as defined in claim 31, wherein the sugar is a sucrose compound, invert sugar, isomerized sugar, glucose, fructose, lactose, malt sugar, D-xylose or isomerized lactose.

33. The process as defined in claim 31, wherein the sugar alcohol is maltitol, sorbitol, mannitol, erythritol, xylitol, lactitol, palatinit, or reduced starch sugar.

34. The process as defined in claim 31 wherein the oligosaccharide is fructooligosaccharide, maltooligosaccharide, isomalto-oligosaccharide, galactooligosaccharide, soy been oligosaccharide, or lactooligosaccharide.

35. The process as defined in claim 23, wherein the edible liquid medium is a suspension comprising at least one aspartyl dipeptide compound in a concentration higher than the solubility the aspartyl dipeptide compound in the edible liquid medium.

36. The process as defined in claim 35, which comprises mixing the at least one aspartyl dipeptide ester compound into the edible liquid medium in an amount higher than the solubility of the aspartyl dipeptide ester compound.

37. The process as defined in claim 35, wherein the mixing is conducted under reduced pressure.

38. The process as defined in claim 35, wherein the edible liquid medium is water or an aqueous solution comprising water and at least one of sugar, sugar alcohol, or oligosaccharide.

39. The process as defined in claim 38, which comprises mixing at least one of aspartyl dipeptide ester compound in the edible liquid medium, and then, mixing therewith at least one compound selected from the group consisting of sugar, sugar alcohol, and oligosaccharide.

40. The process as defined in claim 39, wherein the mixing with at least one compound selected from the group consisting of sugar, sugar alcohol, and olisaccharide is in the presence of water.

41. The process as defined in claim 39, wherein the mixing with at least one compound selected from the group consisting of sugar, sugar alcohol, and olisaccharide is in the absence of water.

42. A liquid composition produced by the process as defined in claim 23.

43. The liquid composition as defined in claim 42, which is in the form of homogeneous suspension.

44. An edible product comprising the liquid composition as defined in claim 42.

45. The edible product as defined in claim 44, which is a sweetener, a food or a beverage.

46. The composition according to claim 20, wherein the sweetness intensity of the aspartyl dipeptide ester compound is more than 4,000 times that of sucrose.

47. The composition according to claim 46, wherein R$_3$ is a hydroxyl group or a methoxy group; and R$_4$ and R$_5$ are hydrogens.

48. The composition according to claim 47, wherein R$_1$ is a hydroxyl group.

49. The composition according to claim 47, wherein R$_1$ is a hydrogen atom.

50. The composition according to claim 48, wherein R$_2$, R$_6$ and R$_7$ are hydrogens.

51. The composition according to claim 48, wherein R$_2$ is a hydrogen atom, a hydroxyl group or a methyl group.

52. The composition according to claim 20, wherein the aspartyl dipeptide ester compound is selected from the group consisting of: (1) a compound wherein R$_1$, R$_4$, R$_5$, R$_6$, and R$_7$ are hydrogen, R$_2$ is OH, R$_3$ is OCH$_3$; (2) a compound wherein R$_1$, R$_2$, R$_4$, R$_5$, R$_6$, and R$_7$ are hydrogen, R$_3$ is OCH$_3$; (3) a compound wherein R$_1$, R$_4$, and R$_5$, are hydrogen, R$_2$ is OH, R$_3$ is OCH$_3$, R$_6$ and R$_7$ are CH$_3$; (4) a compound wherein R$_1$, R$_4$, and R$_5$ are hydrogen, R$_2$ is CH$_3$, R$_3$ is OH, R$_6$ and R$_7$ are CH$_3$; (5) a compound wherein R$_1$, R$_2$, R$_4$, and R$_5$ are hydrogen, R$_3$ is a OCH$_3$, R$_6$ and R$_7$ is CH$_3$; (6) a compound wherein R$_1$, R$_2$, R$_4$, and R$_5$ are hydrogen, R$_3$ is OH, R$_6$ and R$_7$ is CH$_3$; (7) a compound wherein R$_1$ is OH, R$_2$, R$_4$, R$_5$, R$_6$, and R$_7$ are hydrogen, R$_3$ is a OCH$_3$; (8) a compound wherein R$_1$, R$_4$, R$_5$, R$_6$, and R$_7$ are hydrogen, R$_2$ is a CH$_3$, R$_3$ is OH; and (9) a compound wherein R$_1$ and R$_3$ are OH, R$_2$, R$_4$, R$_5$, R$_6$ and R$_7$ are hydrogen.

53. The composition according to claim 20, wherein the solid filler is at least one of the compounds selected from the group consisting of sugar, sugar alcohol, oligosaccharide and polysaccharide.

54. The composition according to claim 53, wherein the sugar is a sucrose compound, invert sugar, isomerized sugar, glucose, fructose, lactose, malt sugar, D-xylose or isomerized lactose.

55. The composition according to claim 53, wherein the sugar alcohol is maltitol, sorbitol, mannitol, erythritol, xylitol, lactitol, palatinit, or reduced starch sugar.

56. The composition according to claim 53, wherein the oligosaccharide is fructooligosaccharide, maltooligosaccharide, isomalto-oligosaccharide, galactooligosaccharide, soy been oligosaccharide, or lactooligosaccharide.

57. The composition according to claim 53, wherein the polysaccharide is glucomannan, dietary fiber, an enzyme decomposition product of guar gum, non-digestible dextrin, polydextrin, starch, dextrin, soluble starch, or modified starch.

58. The composition according to claim 20, wherein the aspartyl dipeptide ester compound is in an amount of from 2 ppm to 95% by weight of the composition.

59. The composition according to claim 20, further comprising drying the solution.

60. The composition according to claim 20, further comprising solidifying the composition.

61. The composition according to claim 60, wherein the solidifying comprise a method selected from the group consisting of condensation drying, spray drying, freeze drying, extrusion granulation and absorption to forming sugar.

62. The composition according to claim 20, wherein the solution comprises a solvent of water, alcohol, or a mixture of water and alcohol.

63. The composition according to claim 20, wherein the mixing comprises homogeneously coating the filler with a solution of the aspartyl dipeptide ester compound.

64. The composition according to claim 20, wherein said composition is a liquid composition.

65. The composition according to claim 20, wherein said composition is a solid composition.

66. The composition according to claim 20, wherein said composition is a paste-like composition.

* * * * *